United States Patent [19]

Orr

[11] Patent Number: 5,752,921
[45] Date of Patent: May 19, 1998

[54] METHOD AND APPARATUS FOR DETERMINING TRACHEAL PRESSURE

[75] Inventor: Joseph A. Orr, Salt Lake City, Utah

[73] Assignee: Korr Medical Technologies, Inc., Salt Lake City, Utah

[21] Appl. No.: 584,892

[22] Filed: Jan. 11, 1996

[51] Int. Cl.[6] ................ A61B 5/085; A61M 16/00
[52] U.S. Cl. ...................... 600/533; 128/207.15
[58] Field of Search .............. 128/716, 204.21, 128/204.23, 204.25, 205.24, 207.14, 207.15

[56] References Cited

U.S. PATENT DOCUMENTS

| | | | |
|---|---|---|---|
| 5,235,973 | 8/1993 | Levinson | 128/207.15 |
| 5,287,851 | 2/1994 | Beran et al. | 128/204.23 |
| 5,487,383 | 1/1996 | Levinson | 128/207.15 |
| 5,546,935 | 8/1996 | Champeau | 128/205.23 |
| 5,582,167 | 12/1996 | Joseph | 128/207.15 |

OTHER PUBLICATIONS

Nicholas A. Wilder et al.; "A System to Calculate Tracheal Pressure from the Endotracheal Tube Cuff"; Abstracts of Scientific Papers Fifth Annual Meeting of the Society for Technology in Anesthesia; Jan. 26, 1995; pp. 258–259.

Nicholas A. Wilder; "A System to Estimate Tracheal Pressure from the Endotracheal Tube Flow and Cuff Pressure"; Dec. 1995; pp. 1–33.

Nicholas A. Wilder et al.; "Evaluation in Animals of a System to Estimate Tracheal Pressure from the Endotracheal Tube Cuff"; pp. 1–21.

Nicholas A. Wilder et al.; "Clinical Trials of a System to Estimate Tracheal Pressure from the Endotracheal Tube Flow"; pp. 1–12.

*Primary Examiner*—Francis Jaworski
*Attorney, Agent, or Firm*—Trask, Britt & Rossa

[57] ABSTRACT

An apparatus and method for using the pressure of the surgical cuff installed surrounding an endotracheal tubes or the flow rate therethrough in the calculation of parameters in lung mechanics.

31 Claims, 3 Drawing Sheets

5,752,921

METHOD AND APPARATUS FOR DETERMINING TRACHEAL PRESSURE

BACKGROUND OF THE INVENTION

1. Field of the Invention

The present invention is related to the apparatus and methods used to determine intra-tracheal pressure and flow for its use in the calculation of parameters in lung mechanics. More specifically, the present invention is related to the apparatus and methods for using surgical cuff pressure of the surgical cuff installed surrounding an endotracheal tube or the flow rate therethrough for use in the calculation of intratracheal pressure for use in lung mechanics calculations, particularly for patients who are connected to a ventilator.

2. State of the Art

Intra-tracheal pressure and flow rate are needed to calculate lung mechanics; i.e., work of breathing, lung compliance, and airway resistance. This is particularly needed concerning patients undergoing surgery and/or in intensive care who are connected to a ventilator. Airway pressure, which is used in such calculation of lung mechanics, is typically measured at the connection between the endotracheal tube and breathing circuit. Problems are encountered under conditions where the air flow of the patient is relatively high in comparison to the diameter of the endotracheal tube thereby causing the pressure drop through the endotracheal tube to be two or three times the intra-tracheal pressure. Such a pressure difference can easily lead to errors in lung mechanics calculations.

During pressure support ventilation, the patient does not perform any work of breathing. The ventilator performs the work of breathing. As such, the ventilator must be set properly for the work of breathing to be performed correctly. Otherwise, the patient may be subject to adverse consequences. Therefore, to set the ventilator properly to do the work of breathing for the patient, the intra-tracheal pressure must be accurately measured or determined to calculate the imposed work of breathing.

In contrast, demand flow ventilation requires the patient to do the work of breathing and create a negative pressure to initiate a breath. During demand flow ventilation, by using intra-tracheal pressure instead of airway pressure measured at the connection between the endotracheal tube and breathing circuit as the triggering pressure decreases the response time in initiating the breath and the patient's work of breathing.

The pressure limits used during pressure control ventilation are determined by the airway pressure. Intra-tracheal pressure can be significantly lower than airway pressure and the pressure difference can change if the intra-tracheal tube becomes blocked or partially blocked with water or mucous or kinked thereby shutting of substantially all flow. Without measuring intra-tracheal pressure, pressure control ventilation can insufficiently ventilate the lungs.

Intra-tracheal pressure can be measured by placing a catheter or catheter-tip pressure transducer down the endotracheal tube. Catheters inserted in the lumen of the endotracheal tube increase the resistance to airflow through the tube, thereby imposing additional work of breathing and distorting the resulting measurements. Alternately, air filled catheters or an extra lumen in the endotracheal tube wall are subject to mucosal blockage and kinking.

Intra-tracheal pressure can be calculated knowing the endotracheal tube diameter and air flow rate. Typically, data is collected in vitro and used to estimate the pressure loss from the endotracheal tube during clinical use in a patient. The calculated pressure loss is subtracted from the airway pressure to stimulate the intra-tracheal pressure. While this technique is convenient and gives continuous measurements, it cannot compensate for kinks in the tube, mucous or mucous plugs in the tube, or obstructions at the tube inlet.

These problems are solved by the present invention.

SUMMARY OF THE INVENTION

The present invention is related to the apparatus and method for using surgical cuff pressure of the surgical cuff installed surrounding an endotracheal tube or the flow rate therethrough in the calculation of parameters in lung mechanics. The present invention uses a non-invasive automatic system and methods for determining intra-tracheal pressure and flow to calculate lung mechanics. The present invention uses either a cuff based technique or a flow-based technique to determine the intra-tracheal pressure.

Figure 1:
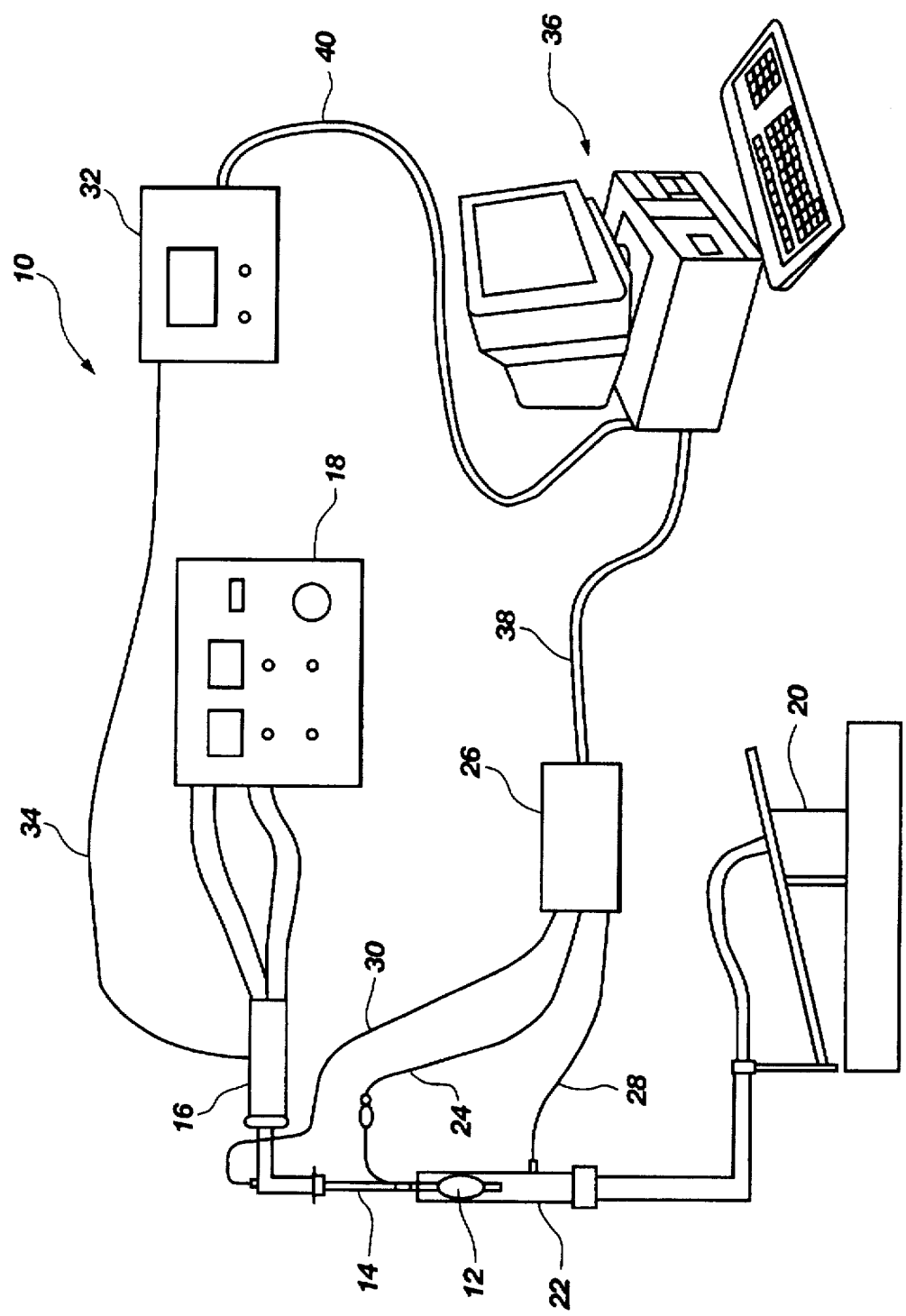
FIG. 1 is a view of the apparatus of the present invention used in a test configuration to simulate testing conditions in animals and humans.

The present invention will be better understood when the drawing figures are taken in conjunction with the detailed description of the invention set forth hereafter.

DETAILED DESCRIPTION OF THE INVENTION

Referring to drawing FIG. 1, the apparatus 10 of the present invention in shown in conjunction with a lung simulator. The apparatus 10 of the present invention comprises a surgical cuff 12 located on a suitable endotracheal tube 14 connected to a flow sensor 16 connected, in turn, to a ventilator 18. To simulate a human lung, a lung simulator 20 is connected to a conduit 22 to which the surgical cuff 12 and endotracheal tube 14 are connected.

The cuff inflation line 24 of the surgical cuff 12 is connected to a suitable pressure sensor of a plurality of pressure sensors 26 to measure the pressure of surgical cuff on a continuous basis. Trachea pressure line 28 is connected to a pressure sensor of a plurality of pressure sensors 26 to measure the pressure of the fluid in the trachea continuously. The pressure of the fluid in the endotracheal tube 14 is continuously measured by a pressure sensor of the plurality of suitable disposable pressure sensors 26 via pressure line 30 prior to the flow sensor 16. The flow sensor 16 is connected to flow meter display 32 via line 34 to display the flow rate of the fluid through endotracheal tube 14 from ventilator 18. The plurality of pressure sensors 26 are connected to a suitable computer 36 via line 38 as well as the flow meter display 32 via line 40. The pressure signals are preferably sampled at 50Hz, although the sampling may occur at a 200 Hz rate, by the use of a 16 bit analog to digital converter. A digital low-pass filter may be used to remove high-frequency noise from the pressure signals being sampled. In this manner, the computer monitors the pressure in the trachea 22, the pressure of the surgical cuff 12, the pressure of the endotracheal tube 14 and the flow rate through the endotracheal tube 14 from the ventilator 18. In a patient, the pressure line 28 and the corresponding press sensor monitoring the trachea pressure are eliminated. If desired, the flow sensor 16, flow meter 32 and their connection 40 to computer 36, may be eliminated.

As previously stated, intra-tracheal pressure can be calculated knowing the diameter of the endotracheal tube 14 and the airflow therethrough. In this instance, the diameter of the endotracheal tube 14 is known before the insertion thereof into a patient. The airflow through the endotracheal tube is measured by the flow sensor 16, calculated by the flow meter 32, and fed into the computer 36. The endotracheal tube or airway pressure is measured via pressure line 30 and a pressure sensor of the plurality of pressure sensors 26. The calculated pressure loss ($\Delta P$) is subtracted from the airway pressure ($P_{aw}$) to estimate the trachea pressure ($P_{trach}$). While this is satisfactory in some instances, it cannot compensate for kinks in the endotracheal tube 14, mucous and mucous plugs therein, or obstructions at the endotracheal tube 14 inlet.

In the present invention, trachea pressure can be measured from changes in the surgical cuff pressure 12 surrounding the endotracheal tube 14. The relationship between the pressure of the surgical cuff 12 and the airway pressure when measured at the start and end of each breath (when the air flow and airway pressure ($P_{aw}$) are zero) is necessary to define the relationship between surgical cuff pressure ($P_{cuff}$) and the trachea pressure ($P_{trach}$). Such relationship between surgical cuff pressure and the trachea pressure is affected by the volume of inflation fluid, typically air, in the surgical cuff 12, the inflation pressure of the surgical cuff 12, and exposed surface area of the distal side of the surgical cuff 12. Once the volume of inflation fluid, inflation fluid pressure, and exposed surface area of distal side of the surgical cuff are known, this relationship allows the pressure of the surgical cuff to be used to determine a calculated continuous measure of the trachea pressure. In this manner, in the first instance of the method of the present invention, the pressure of the surgical cuff is used to accurately calculate the trachea pressure.

Figure 2:
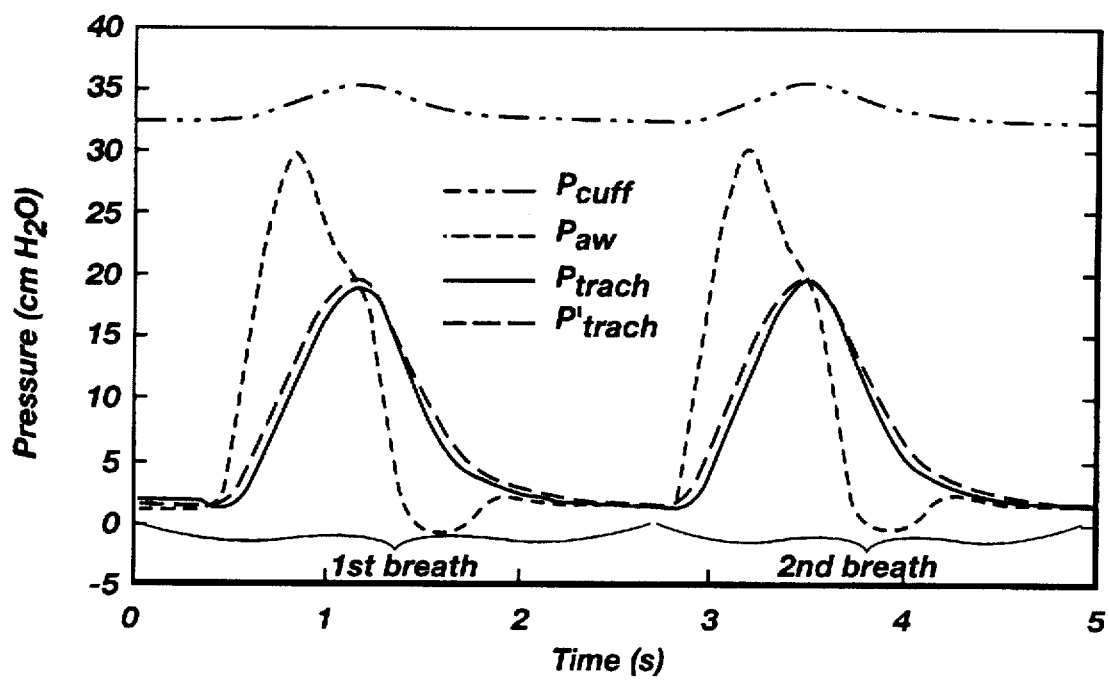
FIG. 2 is a graph of the various pressures measured by the apparatus of the present invention shown in drawing FIG. 1 during two breath cycles.

Referring to drawing FIG. 2, during pressure support ventilation the airway pressure equals tracheal pressure twice during each breath of a patient, at the end of inspiration and at the end of expiration as air is not flowing through the endotracheal tube and there is no pressure drop across the tube. Airway pressure ($P_{aw}$) is measured at these two points, which are typically at zero pressure, and is used to calibrate the relationship between surgical cuff pressure ($P_{cuff}$) and tracheal pressure ($P_{trach}$). Using a suitable pneumotach pressure transducer, such as a Fleisch 18 mm diameter and Validyne CD 12 differential pressure transducer, to measure airway flow and to identify the end-inspiratory and end-expiratory pause, by detecting when the flow is momentarily stopped and then reversed, airway pressure ($P_{aw}$) and cuff pressure ($P_{cuff}$) measured at these points can be used to determine the slope (m) and any offset (b) of a linear relationship between cuff pressure and tracheal pressure.

Figure 3:
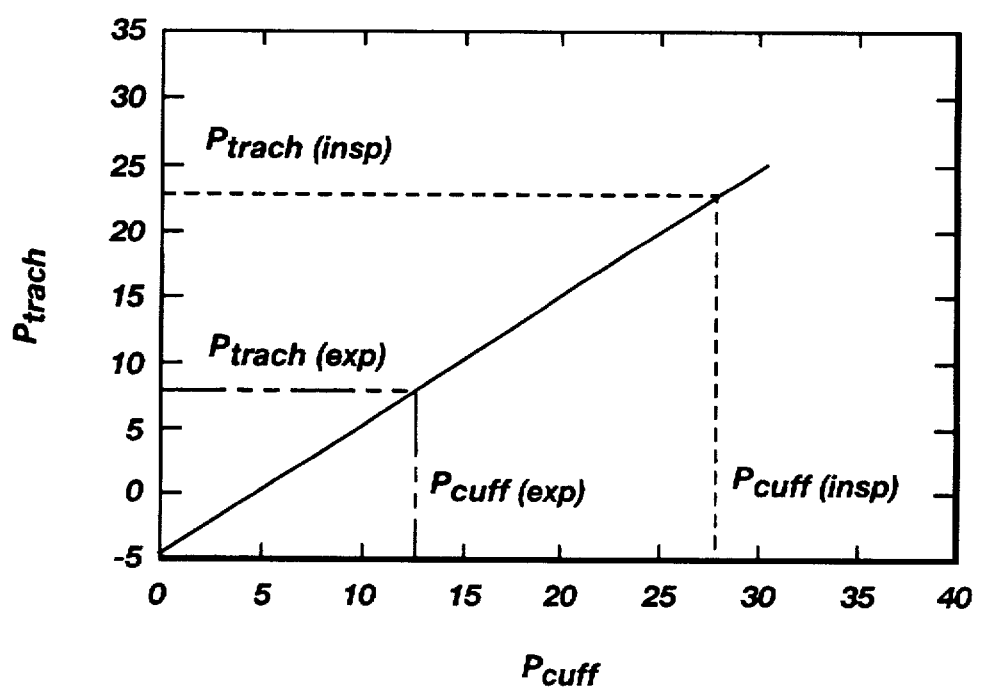
FIG. 3 is a graph of the relationship of some of the pressures measured by the apparatus of the present invention shown in drawing FIG. 1 used in the methods of the present invention.

Referring to drawing FIG. 3, the relationship between the airway pressure ($P_{aw}$) and cuff pressure ($P_{cuff}$) is shown. The calculated tracheal pressure is expressed as tracheal pressure equals slope (m) times cuff pressure plus the offset (b) from the origin.

$$P'_{trach} = M \cdot P_{cuff} + b$$

While the relationship between cuff pressure ($P_{cuff}$) and tracheal pressure ($P_{trach}$) is non-linear and may be modeled by non-linear equations having higher order terms, over small changes in cuff pressures during a breath, a linear model is an adequate approximation. It should be noted that cuff pressure ($P_{cuff}$) may change slightly from one breath to the next due to nitrous oxide diffusion into the cuff and stress relaxation in the material of the cuff; therefore, the slope (m) and offset (b) are recalculated each breath of the method of the present invention to estimate tracheal pressure on each subsequent breath.

To verify the method the apparatus shown in drawing FIG. 1 was used with the ventilator being set at twelve (12) breaths per minute, twenty percent (20%) inspiration time, twenty percent (20%) inspiratory pause time, and zero PEEP. The lung simulator was set with a compliance of 0.06L/cm $H_2O$ and one parabolic resistor (Rp50) in the breathing circuit. Endotracheal tubes having sizes of 4, 5, 6, and 8 mm in PVC tubing having internal diameters of 13, 15, 17, 19 and 22 mm were used. Tidal volumes ranging from 150mL to 750mL were used. Cuff inflation pressures ($P_{cuff}$) of 10, 20, 30, 40, 60, 80, and 100 cm $H_2O$ were used. The tests were performed at 0 % and 10 % inspiratory pause time in several cases in addition to the 20 % used in all other tests.

The maximum difference between calculated tracheal pressure ($P'_{trach}$) and tracheal pressure ($P_{trach}$) for each breath was measured and the difference therebetween was used to calculate the percent error in the tracheal pressure estimate, $$\frac{P'_{trach} - P_{trach}}{P_{trach}} * 100\%,$$

and the maximum percent difference between airway pressure and tracheal pressure, $$\frac{P_{aw} - P_{trach}}{P_{trach}} * 100\%.$$

Figure 4:
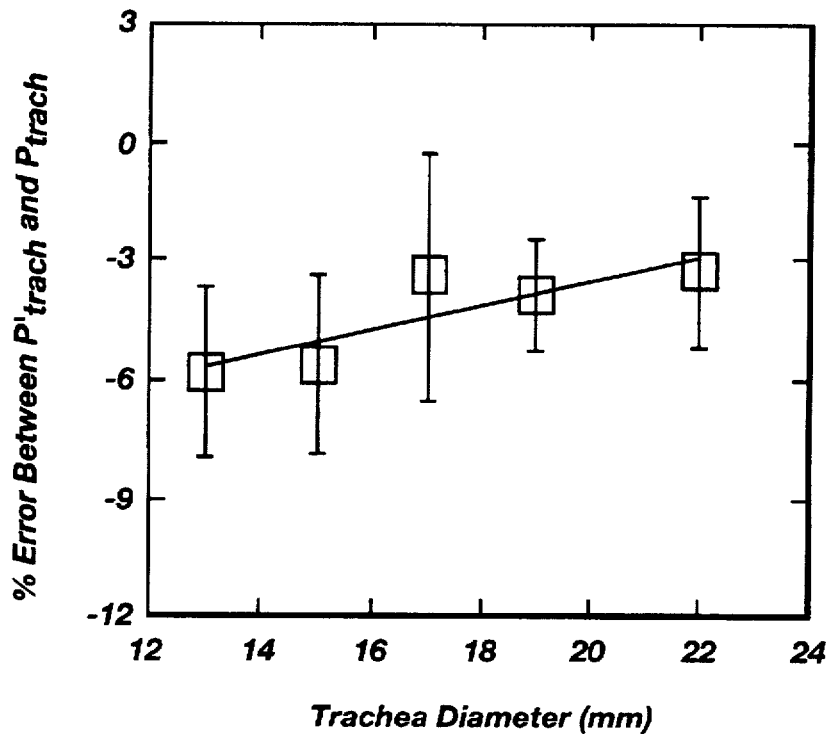
FIG. 4 is a graph of the percent error between the calculated tracheal pressure and the measured tracheal pressure of the present invention.

Referring to drawing FIG. 4, as shown when an endotracheal tube is placed in a smaller trachea, since less area of the cuff is exposed to the tracheal pressure, the calculated tracheal pressure ($P'_{trach}$) is less accurate. The slope of the relationship between the error of the calculated tracheal pressure and tracheal diameter is statistically significant (p is less than 0.01).

Unlike prior art measurement techniques using air or fluid filled catheters to directly measure tracheal pressure, the present invention does not interfere with gas flow, is not subject to blockage, does not require an extra catheter, or additional time during setup.

In the present invention, if the patient is moving or the endotracheal tube is moved, the relationship between cuff pressure and measured tracheal pressure and calculated tracheal pressure will be recalculated on a subsequent breath so that only one (1) to three (3) breaths may be miscalculated. If cuff inflation pressure is dramatically changed, as by reinflating the cuff or by patient movement, the cuff pressure may drift over a few breaths due to the stress relaxation of the cuff material before returning to an accurate quantity for use in the present invention enabling an accurate calculated tracheal pressure ($P'_{trach}$) to be made. As can be easily seen from the foregoing, while nitrous oxide can diffuse into the cuff and increase pressure of the cuff, the increase in cuff pressure is slow and does not cause a significant error in the calculated tracheal pressure ($P'_{trach}$) for each subsequent breath.

It should be noted that it is necessary to prevent leakage around the cuff, or termed cuff leakage, by maintaining cuff pressure sufficiently high in order to obtain accurate results with the present invention. Such cuff leakage may generally be detected in patients by listening to the trachea. In general anesthesia, nitrous oxide diffusion into the cuff is detected by observing an increase of cuff pressure thereby reducing the opportunity for leakage around the cuff pressure thereby reducing the opportunity for leakage around the cuff. Leakage around the cuff may also be observed by detecting a decrease in cuff pressure during end-inspiratory pause, rather than remaining at a constant level throughout the pause.

If desired, a pressure controller can be used to maintain the cuff pressure constant during use to improve the accuracy of the calculated tracheal pressure for use in lung mechanics calculations.

The present invention is useful in the detection of blockage of the endotracheal tube since any significant change over time of the calculated tracheal pressure and airway pressure is readily apparent and may be displayed on the computer monitor.

While the present invention of using measured cuff pressure to calculate a tracheal pressure provides a reliable, accurate calculated tracheal pressure ($P'_{trach}$), noise in the measurement of the cuff pressure may cause errors in the calculated tracheal pressure ($P'_{trach}$), particularly during patient movement and cuff reinflation. Also, the calculation of tracheal pressure is not suited for use during spontaneous patient breathing as cuff pressure drifts from breath to breath requiring the frequent recalibration of the relationship between cuff pressure and measured tracheal pressure.

As an alternative to the calculation of the tracheal pressure based upon cuff inflation pressure, tracheal pressure can be calculated from the pressure drop ($\Delta P_{ETT}$) induced by the endotracheal tube and the airway pressure ($P_{aw}$). That is, tracheal pressure equals airway pressure minus the pressure drop across the endotracheal tube.

$$P_{trach} = P_{aw} - \Delta P_{ETT}$$

It is known that the pressure drop across the endotracheal tube ($\Delta P_{ETT}$) depends upon the amount of flow therethrough. For turbulent flow through a rough-walled straight pipe, the pressure loss of the pipe due to fluid friction with the pipe wall is proportional to the flow squared therethrough ($\dot{Q}^2$).

$$\Delta P_{pipe} = k\dot{Q}^2$$

Since condensation and mucous coat the wall of the endotracheal tube, at high flow conditions the endotracheal tube simulates that of a straight rough walled pipe.

Figure 5:
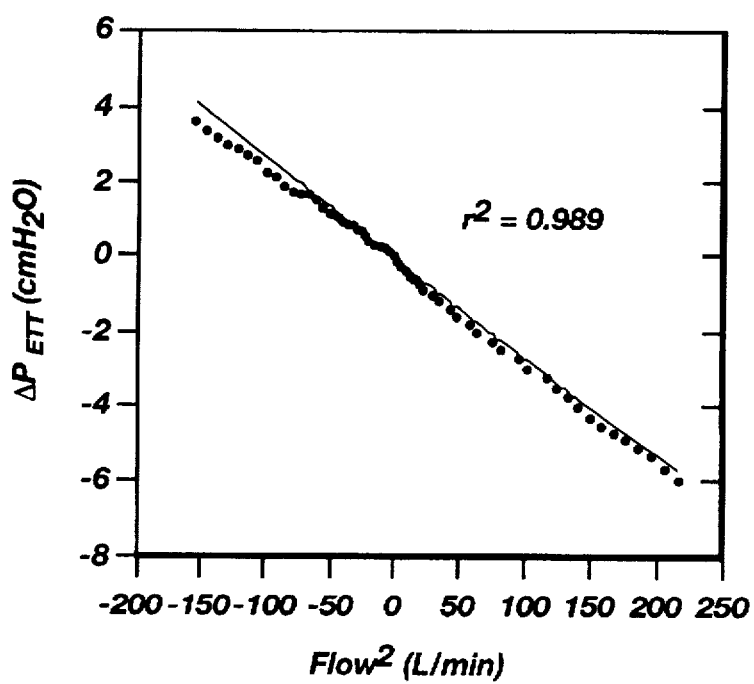
FIG. 5 is a graph of the relationship of the pressure loss across the endotracheal tube in comparison to the flow rate therethrough when squared of the present invention.

Referring drawing FIG. 5, it can be seen that the pressure loss through the endotracheal tube ($\Delta P_{ETT}$) is also proportional to the square root of the flow rate therethrough. This fact can be used in modeling the pressure loss through the endotracheal tube.

Therefore, the pressure drop across the endotracheal tube can be mathematically expressed as proportional to a flow coefficient k1 times the flow rate raised to as second flow rate coefficient k2.

$$\Delta P_{ETT} = k1 \dot{Q}^{k2}$$

The flow coefficients k1 and k2 are calculated from data collected in vitro being then used to estimate the pressure loss across the endotracheal tube in vivo. It has been found that the value of the flow coefficient k1 ranges from 0.18 to 0.067 cmH$_2$O*min/L for endotracheal tubes having a seven millimeter (7mm) to nine millimeter (9mm) diameters while the value of k2 has been found to be approximately 1.95 during inspiration and approximately 1.8 during expiration. Based upon these results a value of 2 may be selected and used to calculate the flow rate through the endotracheal tube for comparison with the measured flow rate therethrough.

However, this mathematical method becomes less accurate when the clinical conditions vary from the in vitro calibration conditions, such as when the endotracheal tube becomes partially blocked or humidity, gas composition and inlet conditions change regarding the patient.

Initially, the pressure loss (drop) through the endotracheal tube ($\Delta P_{ETT}$) can be found by the cuff pressure estimation technique described hereinbefore by subtracting the calculated tracheal pressure ($P'_{trach}$) from the measured airway pressure ($P_{trach}$). This pressure drop and the measured flow can be used to solve for the flow coefficients k1 and k2 described hereinbefore, which are then used to calibrate the flow-base model of the pressure loss of the endotracheal tube. After such calibration, this type of system will work during intermittent spontaneous breathing, using occasional mechanical breaths to maintain calibration; i.e., either controlled mechanical ventilation with end-inspiratory pause (CMV) or synchronized intermittent mandatory ventilation (SIMV).

The flow based model technique for determining intratracheal pressure for the calculation of lung mechanics uses the same general equipment described regarding drawing FIG. 1 hereinbefore which is used in the cuff pressure measurement technique to calculate the tracheal pressure. As previously stated, if desired, the data sampling rate may be increase to 200 Hz from 50 Hz as described hereinbefore.

At each point sampled, the pressure loss of the endotracheal tube ($\Delta P_{ETT}$) is calculated for the measured flow. The cuff pressure measurement calculation technique is used to measure the pressure loss through the use of the equation wherein the pressure loss of the endotracheal tube equals the calculated tracheal pressure ($P'_{trach}$) minus the airway pressure ($P_{aw}$). At the end of each breath, the best linear fit between the pressure loss of the endotracheal tube and the velocity squared therethrough are used to calculate the flow coefficient k1.

After this initial calibration, in the flow based model technique the calculated tracheal pressure ($P'_{trach}$) is calculated as being equal to the airway pressure ($P_{aw}$) minus the flow coefficient k1 times the flow rate (Q) squared.

$$P'_{trach} = P_{aw} - k\dot{Q}^2.$$

At this point the flow coefficient k1 is modified at each breath by adding twenty percent (20%) of the new value to eighty percent (80%) of the old or previous value of the flow coefficient. Where the symbol n is the breath number, the equation may be expressed as:

$$k_n = 0.2k_n + 0.8k_{n-1}.$$

The use of this equation helps suppress spurious data and reduces the time of response of the system when conditions are changing in the endotracheal tube.

The difference between the airway pressure ($P_{aw}$) and the calculated tracheal pressure ($P'_{trach}$ as determined by the cuff estimation technique) at the end of inspiration is stored for five (5) consecutive breaths. If the statistical standard deviation of the data set is above a predetermined threshold (typically 5 cmH$_2$O), the data set is likely to contain spurious cuff pressure estimations. The following equation is used as the criteria for spurious data where i ranges form the value of 1 to 5:

$$\sqrt{\frac{\Sigma\left[(P_iaw - P_i\text{'trach}) - \frac{(\Sigma(P_iaw - P_i\text{'trach}))}{5}\right]^2}{4}} > 5 \text{ cmH}_2\text{O}$$

In this instance, the flow data and pressure loss data of the endotracheal tube from the last breath are rejected and k is not modified.

The preceding equation may also be used as an alarm for the situation where the endotracheal tube pressure loss as calculated using the flow based model technique exceeds a predetermined criteria.

In a situation where the endotracheal tube has become blocked or kinked, the change in pressure loss of the endotracheal tube as calculated by the cuff pressure model technique or the flow based model technique may be used as an alarm. In such an instance the change in endotracheal tube pressure loss is calculated as:

$$\text{change in } \Delta PETT = \frac{\Delta PETT - \text{Min}\Delta PETT}{\text{Min}\Delta PETT} * 100\%$$

Where Min$\Delta P_{ETT}$ is the minimum observed $\Delta P_{ETT}$ for that patient and endotracheal tube combination.

Referring again to drawing FIG. 5, the relationship between the pressure loss of the endotracheal tube and the flow squared ($Q^2$) is shown to be linear for all tubes tested and flow rates tested. The linear regression of the data has a correlation coefficient of 0.989 indicating a good fit for the linear relationship. Shown in the data set forth in FIG. 5 is the test data for a 6.5 millimeter diameter endotracheal tube tested at flow rates from −12.7 to 15.0 liters per minute of flow. Although the relationship between the pressure loss of the endotracheal tube and the flow squared has been illustrated, other flow parameters related to the flow through the endotracheal tube during respiration of a patient may be used.

The flow-based model technique of calculating tracheal pressure (P'$_{trach}$) is less susceptible to noise in the measurement of cuff pressure and is better able to suppress spurious data compared to the cuff pressure model technique. However, since the cuff pressure model technique is required to calibrate the flow-based model technique, the flow-based model technique is not applicable to pure spontaneous breathing. It should be noted that the flow-based model technique does work in the simultaneous intermittent ventilatory mode (SIMV) which is commonly used in the intensive care unit. In this mode, the patient takes complete spontaneous breaths and initiates mechanical breaths. The flow-based model technique also remains accurate when a patient is coming out of anesthesia, and starts to breath spontaneously. In contrast, since the cuff based model technique is not sensitive to changes in Reynolds number effects or endotracheal tube conditions, it can adjust to variable clinical circumstances.

From the foregoing it is evident that the results for both measurement systems are accurate for clinical use. Both measurement systems have similar errors when compared to actual tracheal pressure (P$_{trach}$); however, only the flow-based model technique works during intermittent spontaneous breathing, is less sensitive to signal noise, and is the better of the measurement techniques.

In contrast to the present invention, there are no other non-invasive systems to measure tracheal pressure (P$_{trach}$) that are capable of adjusting to variable clinical conditions. While measurement probes or catheters can be inserted down the lumen of an endotracheal tube, such change the characteristics of the endotracheal tube. Systems that are calibrated in vitro can present misleading data when used in vivo.

Benefits of the present invention are that cuff pressure is known thereby allowing the clinician to avoid the problems associated with high cuff pressures and any associated problems during surgery. Furthermore, with the use of alarms the present invention is capable of automatically recognizing kinked or blocked endotracheal tubes or occlusions in such tubes thereby helping to eliminate associated problems.

It will be understood that additions, changes, modifications, or deletions may be made to the present invention which fall within the scope thereof.

What is claimed is:

1. An apparatus for the non-invasive measuring the tracheal pressure in the trachea of a patient during the respiration of said patient, said apparatus comprising:

an endotracheal tube having an inflatable surgical cuff therearound, an inlet, an outlet, and a bore therethrough, the inflatable surgical cuff engaging a portion of trachea of a patient;

a first pressure sensor for sensing the pressure of a fluid flowing through the endotracheal tube during the respiration of a patient;

a second pressure sensor connected to the inflatable surgical cuff of the endotracheal tube for sensing the pressure therein during the respiration of a patient; and computing apparatus connected to the first pressure sensor and connected to the second pressure sensor for computing the tracheal pressure in the bore of the endotracheal tube from said first pressure of said fluid flowing through said endotracheal tube during the respiration of a patient and from said second pressure sensor connected to the inflatable surgical cuff of said endotracheal tube sensing said pressure therein during the respiration of a patient.

2. The apparatus of claim 1, wherein said apparatus further comprises:

a flow measurement apparatus having an inlet and an outlet thereof, the flow measurement apparatus being connected to the endotracheal tube to measure the flow through said endotracheal tube during the respiration of a patient.

3. The apparatus of claim 1, wherein said apparatus further comprises:

ventilation apparatus for supplying fluid under pressure to a patient during the respiration thereof, the ventilation apparatus connected to the endotracheal tube having an inflatable surgical cuff therearound.

4. The apparatus of claim 1, wherein the flow measurement apparatus includes:

apparatus for calculating the flow of fluid through the endotracheal tube to and from a patient during the respiration thereof.

5. A method of non-invasively measuring the pressure of the flow of fluid through the trachea of a patient during the respiration thereof, said method comprising the steps of:

providing an endotracheal tube having an inflatable surgical cuff therearound, an inlet, an outlet, a bore therethrough;

inserting the endotracheal tube into said trachea of a patient;

inflating the inflatable portion of the endotracheal tube to engage a portion of said trachea of a patient using a second fluid;

measuring the pressure of said flow of said fluid during said respiration of a patient at a location outside a patient;

measuring the pressure of the fluid contained within the inflatable surgical cuff of the endotracheal tube after the inflation thereof during said respiration of a patient; and determining said pressure of said fluid in the bore of the endotracheal tube during said respiration of a patient using the pressure of the second fluid in the inflatable portion of the surgical cuff, the pressure of said fluid at a location outside a patient, and the flow rate of said fluid during said respiration of a patient.

6. The method of claim 5, wherein said method further comprises the step of:

measuring the flow of the fluid flowing through the endotracheal tube.

7. The method of claim 5, wherein said method further comprises the step of:

measuring the flow of the fluid flowing through the endotracheal tube; and determining periods of zero flow through the endotracheal tube.

8. The method of claim 5 wherein the inflatable surgical cuff is inflated to a pressure slightly higher than the pressure of the fluid of a patient below the location of the endotracheal tube in the trachea of a patient.

9. The method of claim 5 wherein the method further comprises the steps of:

predetermining the size of the bore of the endotracheal tube to provide a low flow rate therethrough during said respiration of a patient.

10. The method of claim 5 wherein the method further comprises the step of:

predetermining the size of the endotracheal tube with respect to a patient such that when the inflatable cuff of the endotracheal tube is inflated in a patient the cross sectional area of the inflated inflatable surgical cuff is as large as possible with respect to a patient without substantial injury thereto.

11. The method of claim 5 wherein the inflatable surgical cuff of the endotracheal tube is inflated to a pressure in the range of substantially 10 to 100 cm of $H_2O$.

12. The method of claim 5 wherein the method further comprises the steps of:

maintaining the pressure of the inflatable surgical cuff of the endotracheal tube at a substantially constant pressure after the inflation thereof.

13. The method of claim 5 wherein the method further comprises the step of:

displaying the pressure of said fluid measured outside a patient during said respiration of a patient.

14. The method of claim 13 wherein the method further comprises the steps of:

displaying the determined pressure of said fluid in the bore of the endotracheal tube.

15. The method of claim 14 wherein the method further comprises the step of:

displaying the difference between the pressure of said fluid measured outside a patient during said respiration of a patient and the determined pressure of said fluid in the bore of the endotracheal tube.

16. The method of claim 5 wherein the method further comprises the step of:

activating a warning indicator if the pressure of the inflatable surgical cuff of the endotracheal tube exceeds a predetermined limit.

17. A method of non-invasively measuring the pressure of fluid in the trachea of a patient during the respiration thereof, said method comprising the steps of:

providing an endotracheal tube having an inflatable surgical cuff therearound, an inlet, an outlet, and a predetermined diameter bore therethrough;

inserting the endotracheal tube into said trachea of a patient;

inflating the inflatable portion of the endotracheal tube to engage a portion of said trachea of a patient using a second fluid;

measuring the pressure of the flow of said fluid during said respiration of a patient at a location outside a patient;

measuring the pressure of the fluid contained within the inflatable surgical cuff of the endotracheal tube after the inflation thereof during said respiration of a patient;

initially determining said pressure of said fluid in the bore of the endotracheal tube during said respiration of a patient using the pressure of the second fluid in the inflatable portion of the surgical cuff, the pressure of said fluid at a location outside a patient, and the flow rate of said fluid during said respiration of a patient;

initially determining the pressure loss of the flow of said fluid through the endotracheal tube by subtracting the pressure of said fluid at a location outside a patient from the initially determined pressure of said fluid in the bore of the endotracheal tube;

determining the relationship between the initial pressure loss of the flow of said fluid determined for the endotracheal tube and a parameter of the flow of said fluid through the endotracheal tube using the measured flow of said fluid;

determining a second pressure loss of the flow of said fluid through the endotracheal tube by calculating a second pressure of said fluid in the bore of the endotracheal tube by subtracting from the pressure of said fluid measured outside a patient the quantity of the measured flow rate of said fluid multiplied by itself and by the relationship between the initial pressure loss determined for the endotracheal tube and a parameter of the flow of said fluid through the endotracheal tube; and calculating a second pressure in the bore of said endotracheal tube using the second pressure loss calculated and the pressure of said fluid outside a patient.

18. The method of claim 17 wherein the inflatable surgical cuff is inflated to a pressure slightly higher than the pressure of the fluid of a patient below the location of the endotracheal tube in the trachea of a patient.

19. The method of claim 17 wherein the method further comprises the steps of:

predetermining the size of the bore of the endotracheal tube to provide a low flow rate therethrough during said respiration of a patient.

20. The method of claim 17 wherein the method further comprises the step of:

predetermining the size of the endotracheal tube with respect to a patient such that when the inflatable cuff of the endotracheal tube is inflated in a patient the cross sectional area of the inflated inflatable surgical cuff is as large as possible with respect to a patient without substantial injury thereto.

21. The method of claim 17 wherein the inflatable surgical cuff of the endotracheal tube is inflated to a pressure in the range of substantially 10 to 100 cm of $H_2O$.

22. The method of claim 17 wherein the method further comprises the steps of:

maintaining the pressure of the inflatable surgical cuff of the endotracheal tube at a substantially constant pressure after the inflation thereof.

23. The method of claim 17 wherein the method further comprises the step of:

displaying the pressure of said fluid measured outside a patient during said respiration of a patient.

24. The method of claim 23 wherein the method further comprises the steps of:

displaying the determined pressure of said fluid in the bore of the endotracheal tube.

25. The method of claim 24 wherein the method further comprises the step of:

displaying the difference between the pressure of said fluid measured outside a patient during said respiration of a patient and the determined pressure of said fluid in the bore of the endotracheal tube.

26. The method of claim 17 wherein the method further comprises the step of:

activating a warning indicator if the pressure of the inflatable surgical cuff of the endotracheal tube exceeds a predetermined limit.

27. The method of claim 17, wherein the method further comprises the step of:

measuring the flow of fluid through the endotracheal tube during said respiration of a patient.

28. The method of claim 17, wherein the parameter of the flow of said fluid through the endotracheal tube is the velocity squared of said flow of said fluid.

29. A method of non-invasively measuring the pressure of fluid in the trachea of a patient during the respiration thereof, said method comprising the steps of:

providing an endotracheal tube having an inflatable surgical cuff therearound, an inlet, an outlet, and a predetermined diameter bore therethrough;

inserting the endotracheal tube into said trachea of a patient;

inflating the inflatable portion of the endotracheal tube to engage a portion of said trachea of a patient using a second fluid;

measuring the pressure of the flow of said fluid during said respiration of a patient at a location outside a patient;

measuring the pressure of the fluid contained within the inflatable surgical cuff of the endotracheal tube after the inflation thereof during said respiration of a patient;

initially determining said pressure of said fluid in the bore of the endotracheal tube during said respiration of a patient using the pressure of the second fluid in the inflatable portion of the surgical cuff, the pressure of said fluid at a location outside a patient, and the flow rate of said fluid during said respiration of a patient;

initially determining the pressure loss of the flow of said fluid through the endotracheal tube by subtracting the pressure of said fluid at a location outside a patient from the initially determined pressure of said fluid in the bore of the endotracheal tube;

determining the relationship between the initial pressure loss of the flow of said fluid determined for the endotracheal tube and a parameter of the flow of said fluid through the endotracheal tube using the measured flow of said fluid;

determining a second pressure loss of the flow of said fluid through the endotracheal tube by calculating a second pressure of said fluid in the bore of the endotracheal tube by subtracting from the pressure of said fluid measured outside a patient the quantity of the measured flow rate of said fluid multiplied by itself and by the relationship between the initial pressure loss determined for the endotracheal tube and a parameter of the flow of said fluid through the endotracheal tube; and calculating a second pressure in the bore of said endotracheal tube using the second pressure loss calculated and the pressure of said fluid outside a patient.

30. The method of claim 29 wherein the inflatable surgical cuff is inflated to a pressure slightly higher than the pressure of the fluid of a patient below the location of the endotracheal tube in the trachea of a patient.

31. The method of claim 29 wherein the method further comprises the steps of:

maintaining the pressure of the inflatable surgical cuff of the endotracheal tube at a substantially constant pressure after the inflation thereof.

* * * * *

UNITED STATES PATENT AND TRADEMARK OFFICE
CERTIFICATE OF CORRECTION

PATENT NO. : 5,752,921
DATED : May 19, 1998
INVENTOR(S) : Orr

It is certified that error appears in the above-identified patent and that said Letters Patent is hereby corrected as shown below:

In column 1, line 54, change "of" to --off--;
In column 2, line 48, change "in" (first occurrence) to --is--;
In column 3, line 11, change "press" to --pressure--;
In column 5, lines 13-14, delete "pressure thereby reducing the opportunity for leakage around the cuff";
In column 5, line 48, change "($\Delta P_{ett}$)" to -- $\Delta P_{ett}$ --
In column 5, line 59, after "Referring" insert --to--;
In column 6, line 38, change "increase" to --increased--;
In column 7, line 18, change "as" to --is--;
In column 7, line 58, change "breath" to --breathe--;
In column 8, line 23, after "measuring" insert --of--;
In column 8, line 28, after "portion of" insert --the--; and
In column 8, line 38, after "pressure" insert --sensor sensing said pressure--.

Throughout the patent, each occurrence of "$\Delta P_{ETT}$" should read -- $\Delta P_{ett}$ --

Signed and Sealed this

Seventh Day of September, 1999

Attest:

Q. TODD DICKINSON

*Attesting Officer*   *Acting Commissioner of Patents and Trademarks*